(12) United States Patent
Taff et al.

(10) Patent No.: US 12,214,207 B2
(45) Date of Patent: Feb. 4, 2025

(54) OPTIMIZED VECTOR SELECTION FOR A MULTI-AXIS ACCELEROMETER IN AN IMPLANTABLE MEDICAL DEVICE

(71) Applicant: BIOTRONIK SE & Co. KG, Berlin (DE)

(72) Inventors: Brian M. Taff, Portland, OR (US); Min Qu, Wilsonville, OR (US); Kurt Swenson, Dayton, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 664 days.

(21) Appl. No.: 17/423,694

(22) PCT Filed: Sep. 18, 2019

(86) PCT No.: PCT/EP2019/074967
§ 371 (c)(1),
(2) Date: Jul. 16, 2021

(87) PCT Pub. No.: WO2020/173582
PCT Pub. Date: Sep. 3, 2020

(65) Prior Publication Data
US 2022/0111214 A1    Apr. 14, 2022

Related U.S. Application Data

(60) Provisional application No. 62/811,556, filed on Feb. 28, 2019.

(51) Int. Cl.
*A61N 1/365* (2006.01)
*A61N 1/372* (2006.01)

(52) U.S. Cl.
CPC ..... *A61N 1/36542* (2013.01); *A61N 1/37247* (2013.01)

(58) Field of Classification Search
CPC ............ A61N 1/36542; A61N 1/36535; A61N 1/3756; A61N 1/36071; A61N 1/36139;
(Continued)

(56) References Cited

U.S. PATENT DOCUMENTS

| 9,522,276 B2 | 12/2016 | Shen et al. |
| 2013/0289652 A1 | 10/2013 | Skelton et al. |

(Continued)

OTHER PUBLICATIONS

International Search Report (PCT/ISA/210) and Written Opinion (PCT/ISA/237) mailed on Dec. 6, 2019, by the European Patent Office as the International Searching Authority for International Application No. PCT/EP2019/074967.

*Primary Examiner* — Jon Eric C Morales
(74) *Attorney, Agent, or Firm* — Buchanan Ingersoll & Rooney PC

(57) ABSTRACT

The present disclosure relates to a medical system, comprising at least an implantable medical device, and a multi-axis accelerometer comprised by the implantable medical device for measuring an acceleration of the implantable medical device along a plurality of vectors, wherein the multi-axis accelerometer is configured to provide for each vector a signal indicative of the acceleration of the implantable medical device in the direction of the respective vector. The medical system is configured to assess said signals to automatically select or propose a vector of said plurality of vectors that comprises the best alignment with a pre-defined vector.

12 Claims, 12 Drawing Sheets

(58) Field of Classification Search
CPC ............ A61N 1/36146; A61N 1/36153; A61N 1/36171; A61N 1/36175; A61N 1/36185; A61N 1/36521; A61N 1/3655; A61N 1/36585; A61N 1/3706; A61N 1/37205; A61N 1/37247; A61N 1/378; A61B 5/1116; A61B 5/1118; A61B 2560/0209; A61B 2562/0219; A61B 5/01; A61B 5/021; A61B 5/024; A61B 5/0816; A61B 5/1121; A61B 5/318; A61B 5/369; A61B 5/389; A61B 5/4836; B81B 2201/0235; B81B 2201/06; B81B 2207/012; B81B 7/0087; B81C 1/00968; G01P 15/00
See application file for complete search history.

(56) References Cited

U.S. PATENT DOCUMENTS

2017/0056664 A1   3/2017   Kane et al.
2017/0113051 A1   4/2017   Sheldon et al.

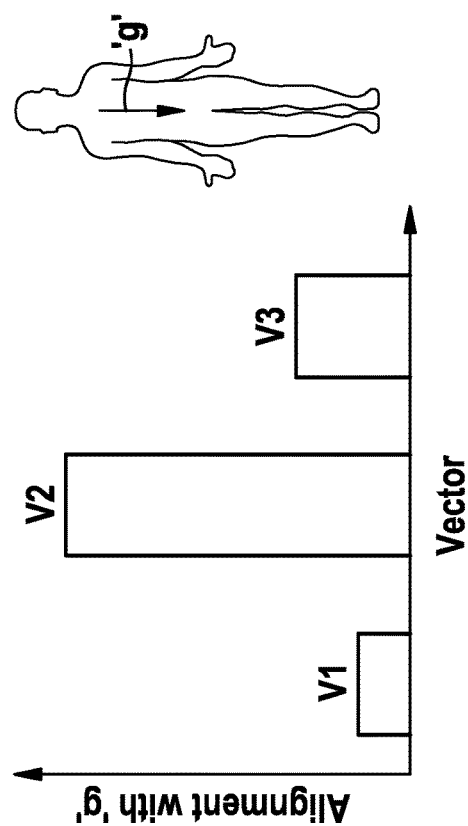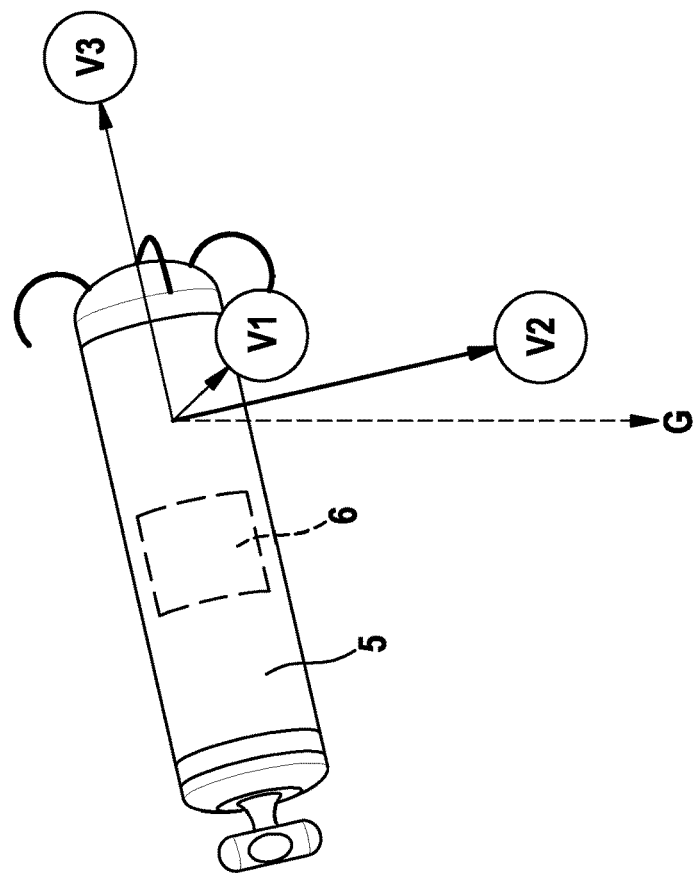
FIG. 2A

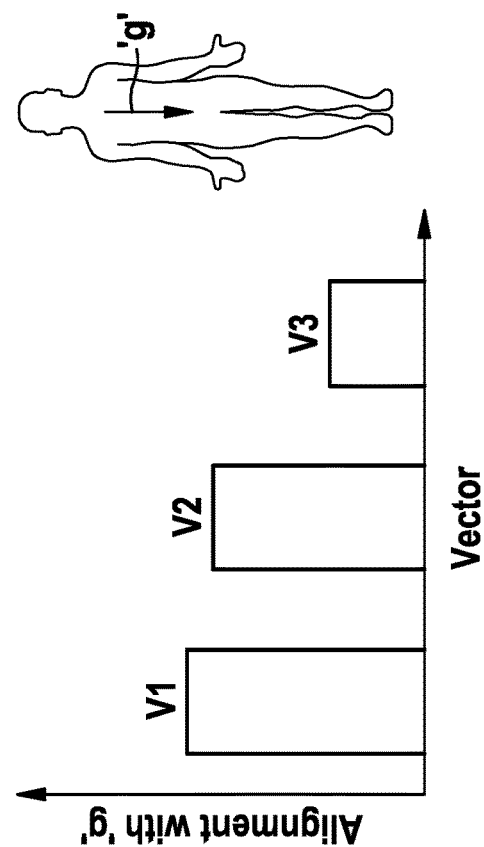
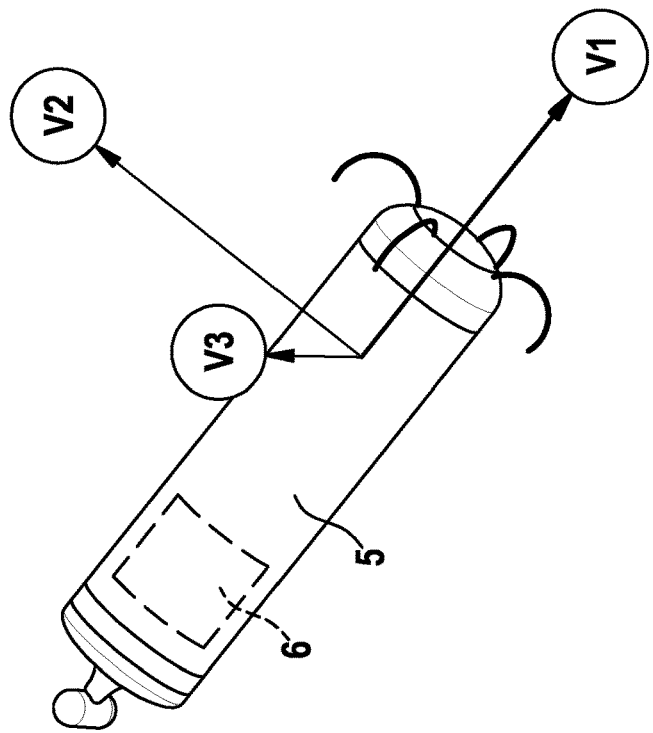
FIG. 2B

Jane Doe (01 Oct 1972) — Export — Support — PSA — 16:29:12 21 June 19 — Therapy ENABLED

72

← Overview

Sensing 03-Jul-2018
Threshold 03-Jul-2018
Impedance 03-Jul-2018
Sensor 03-Jul-2018

▸ Show All Channels

Therapy Program

| | |
|---|---|
| Vector selection | Vector 1 |
| Sensor gain | Auto |
| Sensor threshold | Medium |
| Basic Rate [bpm] | 50 |
| Max Activate Rate | 120 |

Activity report

Heart rate during activity (bpm)
180
120
80
40
0
heart rate in bpm
00:00                                05:59

Vector 2 selected

Sensor test

To make sure the activity vector is appropriate, configure your therapy settings on the left and tap the start button to begin the guided test. To interrogate without running the test, tab the interrogate button.

▲ Start Test
Interrogate

Copy to Program

⊕ Adjust Parameters

OPTIMIZED VECTOR SELECTION FOR A MULTI-AXIS ACCELEROMETER IN AN IMPLANTABLE MEDICAL DEVICE

CROSS-REFERENCE TO RELATED APPLICATIONS

This application is the United States national phase under 35 U.S.C. § 371 of PCT International Patent Application No. PCT/EP2019/074967, filed on Sep. 18, 2019, which claims the benefit of U.S. Patent Application No. 62/811,556, filed on Feb. 28, 2019, the disclosures of which are hereby incorporated by reference herein in their entireties.

TECHNICAL FIELD

The present disclosure relates to a medical system and to a corresponding method.

BACKGROUND

Some implantable medical devices (IMDs) comprise an accelerometer for the detection of motion/activity of a patient, e.g. to adapt the pacing rate of a pacemaker when increased activity of the patient is detected.

Multi-axis accelerometers enable the detection of motion with an ability to best measure such motion through the collection of data acquired by the on-chip axis (or axes) best aligned with a motion vector of interest. In a simplest form, data gathered from a single axis demands the least system overhead (e.g. current budgeting, computation, etc.) to report motion in a specified direction (or anti-direction, since the polarity of the motion along the axis is not important). Alternatively, in cases where no single on-chip axis aligns well with the motion direction of interest, data collected from a multitude of axes can be computationally combined (e.g. via weighting, vector math, etc.) to report data that best aligns a mathematically-generated vector with the motion direction of interest.

Regardless of the approach, gravity presents a prevailing downward acceleration vector to the implant which effectively generates an additive "DC offset" (DC—direct current, AC—alternating current) response to signaling gathered from any accelerometer axis aligned with the gravitational vector. Surveying each of the accelerometer chip's axes in a "motion free" condition and assessing their baseline amplitudes can readily facilitate determining which axis or combination of axes align with this gravitational vector. Such information is often enough to select which vector is preferable for product feature support.

Presently, selection of the accelerometer vectors within implantable medical devices (IMDs) is either established as a "hard coded" configuration during product development and/or factory configurations or it employs clinician follow-up interactions that demand the vector to be chosen following the execution of a series of patient motions/exercises and an analysis of resultant generated data. The former process demands ample insight during product development to pick a vector likely to serve a bulk of the patient population. The approach thereby denies catering of the response to individual needs. In the alternative follow-up based approach, a time consuming process is mandated. In presently known devices a single vector is selected for data collection and then a motion/exercise routine is performed by the patient. To assess the effects on multiple axes, the routine must be repeated for each of the available on-chip axes. Each cycle in this iterative process can typically require no fewer than 15 minutes of in-clinic follow-up time. Once all of the axes have been assessed it then becomes possible to select an optimal vector. For a 3-axis accelerometer, such a process would thereby demand ~45 minutes (3-axis times 15 min). This duration challenges access to optimized patient care as not everyone is able to sustain protracted physical activities for such spans and clinical resources are often limited.

Furthermore, sequential testing (i.e. one vector at a time) is not guaranteed to prove identical results from one round to the next and therefore the gathered results from one vector may not be well suited for direct comparison to another. As such, the procedure is often skipped, a default value is selected and, if the orientation of the IMD is such that the default is inappropriate, any dependent features do not operate at their intended performance level.

The in-patient orientation of an IMD is often unique. For implantable cardiac monitors (ICMs) and leadless pacemaker systems this condition is compounded compared to pocket-based implants which are most often stationed within the patient anatomy in a known, lead ports up position and regularly held in place via through-device suturing processes. The multitude of implant sites compatible with ICMs and leadless pacemaker systems mean that determining which axis of an in-device multi-axis accelerometer best aligns with gross physiological references (e.g. a head-to-toe vector) critical to affiliated feature support, is more of a challenge.

With regard to the drawbacks described above, a problem to be solved can be seen in shorten the duration and complexity of in-clinic procedures needed to determine the "best" in-device accelerometer vector.

The present disclosure is directed toward overcoming one or more of the above-mentioned problems, though not necessarily limited to embodiments that do.

SUMMARY

Particularly, the present disclosure details a scheme whereby the implant may execute a routine to assess signaling on each of the vectors and enable optimized selection of the accelerometer axis best paired with feature sensing needs. This support can be enabled either as an automated (and potentially adaptive) routine for feature support between follow-up or one that supports ease in clinical workflow during follow-up to select or promote an optimized vector through the relay of critical metrics to a user via a GUI presentation.

Particularly, further objectives can be seen in one or more of the following objectives:

expand the ability to support vector optimization to scenarios where the patients are physically limited and face challenges in completing the 'exercise' test (i.e., cannot walk or perform other required exercise for upwards of 45 min), offer improved GUI reporting of IMD accelerometer responses to better inform the clinician on the trade-offs in effect when selecting the "best" in-device accelerometer vector, provide improved sensing of accelerometer-based inputs for related IMD feature support and thereby improved patient experience with the IMD between follow-up, and offer a means for periodically assessing the accelerometer vector between follow-up and adapting the selection if alternative choices emerge as preferential.

A medical system and method according to the respective independent claims are provided.

In one aspect, a medical system is disclosed, comprising at least an implantable medical device, and a multi-axis accelerometer comprised by the implantable medical device for measuring an acceleration of the implantable medical device along a plurality of vectors (also denoted acceleration vectors or axes herein), wherein particularly the multi-axis accelerometer is configured to provide for each vector a signal indicative of the acceleration of the implantable medical device in the direction of the considered vector.

The medical system (particularly the medical implant device) is configured to assess said signals to automatically select or propose a vector out of said plurality of vectors of the accelerometer that comprises the best alignment with a pre-defined vector.

Particularly, this selected or proposed vector is the one having the largest component in the direction of the pre-defined vector among the plurality of said vectors.

Particularly, said plurality of vectors comprises or consists of three orthogonal or linearly independent vectors (e.g. in x, y and z direction).

Particularly, the system, particularly the implantable medical device, is configured to measure an acceleration of the implantable medical device during operation of the device in the direction of the selected (or proposed) vector.

The implantable medical device may be configured to collect data when the patient's posture is prescribed to be stationary in a specific position (e.g. a standing position or a sitting position). The collected data may comprise for each vector (V1, V2, V3) at least a DC signal of the accelerometer being indicative of the acceleration of the implantable medical device in the direction of the respective vector (V1, V2, V3), wherein the selected or proposed vector is the one associated with the signal having the largest amplitude among the signals.

According to an embodiment of the medical system, the medical system may consist of the implantable medical device alone which automatically selects the accelerometer vector. However, the system may comprise additional devices that may interact with the implantable medical device (also denoted as implant herein).

In other words, the present disclosure details a scheme whereby the implant may execute a routine to assess signaling on each of the vectors and enable optimized selection of the accelerometer axis/vector best paired with feature sensing needs. This support can be enabled either as an automated (and potentially adaptive) routine for feature support between follow-up or one that supports ease in clinical workflow during follow-up to select or promote an optimized vector through the relay of critical metrics to a user via a GUI presentation.

In an embodiment, the implantable medical device comprises the ability to acquire data from any one of the multiple accelerometer axes/vectors as an automaticity and/or a triggered response.

Further, in an embodiment, the implant comprises the capacity to determine the best accelerometer axis/vector for targeted feature support (especially rate adaptation) based upon the data collected from the multitude of accelerometer axes/vectors.

Furthermore, according to an embodiment, the implantable medical device is configured to collect data when the implantable medical device is moved along the pre-defined vector, wherein the collected data comprises for each vector at least a signal of the accelerometer being indicative of the magnitude of the acceleration of the implantable medical device in the direction of the vector, wherein the selected or proposed vector is the one associated with the signal having the largest amplitude among the signals.

Further, according to an embodiment, the implantable medical device is one of: an intracardiac pacing system (also called implantable leadless pacemaker); an implantable cardiac monitor (also called loop recorder); and an implantable pulse generator (IPG) for neurostimulation.

Particularly, in case the implantable medical device is an intracardiac pacing system, the latter is preferably configured to automatically select and/or adapt the accelerometer vector used for rate adaptation based on the signals from the accelerometer.

Furthermore, according to an embodiment, in case the implantable medical device is an intracardiac pacing system, the implantable medical device is configured to generate and apply pacing pulses to the heart of a patient at a rate, wherein the implantable medical device is configured to adapt said rate depending on an acceleration of the implantable medical device with respect to said selected or proposed vector.

According to an embodiment, the pre-defined vector is the gravitational vector, i.e. the direction of gravity.

Furthermore, in an embodiment, the system or implantable medical device comprises the ability to collect data from each of the multiple accelerometer axes/vectors in sequentially scanned format.

Furthermore, in an embodiment, the medical system or the implantable medical device is configured to collect said data or signals from each of the multiple accelerometer vectors in a sequential fashion. Particularly, the medical system/implantable medical device cycles through each vector one after the other and thereby acquires the amplitude of the respective signal of the accelerometer for each vector. Further, in an embodiment, the implantable medical device is configured to store the collected data in the medical implant device.

Furthermore, according to an embodiment, the system is configured to conduct an activity test during which the patient performs an exercise for a pre-defined amount of time, wherein the implantable medical device is configured to sample the heart rate of the patient, and to adapt a rate of the pacing pulses of the implantable medical device based on the acceleration of the implantable medical device with respect to said selected or proposed vector.

Particularly, according to an embodiment, the implantable medical device comprises the ability to store data within the implant detailing the activity response of any surveyed accelerometer vector.

Furthermore, according to an embodiment, the medical system comprises a monitoring device (e.g. a Holter device) configured to be placed outside a body of the patient, wherein the implantable medical device is configured to transmit the collected data to the monitoring device. Particularly, the monitoring device is a heart monitoring device for monitoring the heart of the patient, wherein particularly the monitoring device is configured to sample an electrocardiogram of the patient.

Thus, the medical system may comprise an option to eliminate implant storage for accelerometer vector or axis signaling and instead stream said data to a patient-worn monitoring device. Particularly, the monitoring device may be capable of collecting the implant-streamed accelerometer vector/axis data for subsequent programmer interrogation.

According to a further embodiment, the medical system comprises a programmer (also denoted as programming device) configured to receive the collected data from the implantable medical device or from the monitoring device, wherein the programmer is configured to assess the collected data to automatically select or propose said vector that comprises the best alignment with said pre-defined vector.

Thus, the programmer of the medical system may comprise the capacity to interpret data gathered by the implant and/or monitoring/Holter device and to compute best accelerometer vector choices for intended feature support (especially rate adaptation).

Furthermore, according to an embodiment, the medical system, particularly the programmer, comprises a graphical user interface (GUI), particularly for configuring, initiating, interpreting exercise and vector optimization tests.

Particularly, the graphical user interface is configured to graphically display the collected data or information derived from the collected data, and/or to display the selected or proposed acceleration vector, and/or to display a picture of the implantable medical device showing the selected or proposed acceleration vector.

Particularly, the medical system, particularly said GUI, comprises the ability to orient a picture of the implantable medical device in accordance with the collected data to highlight which acceleration vector is best aligned with the pre-defined vector (e.g. the gravitational vector). Particularly, the GUI is configured to show the comparative alignments of acceleration vector response data to the pre-defined vector (e.g. gravitational vector), including the promotion of a single acceleration vector as a best choice.

Furthermore, according to an embodiment, the graphical user interface is configured to perform at least one of:
  receive input by a user to let the programmer or the system automatically select said vector of said plurality of vectors that comprises the best alignment with the pre-defined vector,
  display information on the available vector configurations to guide user insight on the one best aligned with the predefined vector,
  receive input by the user to confirm the proposed vector as the selected vector (or receive input by the user to select another accelerometer vector),
  receive input by a user to initiate an activity test during which the patient performs an exercise for a pre-defined amount of time and the implantable medical device records the heart rate of the patient and/or the raw activity signal output from the accelerometer, wherein a rate adaption of the pacing pulses by the implantable medical device is based on the acceleration of the implantable medical device with respect to said selected or proposed vector,
  display the heart rate and/or raw activity signal output recorded during the activity test (e.g. as one or more trend plots),
  receive input by a user to change a therapy program setting of the implantable medical device, and
  display a preview of an expected heart rate response for the changed therapy program setting.

Furthermore, in an embodiment, the programmer comprises a capacity to retain/display information on "before" and "after" exercise and vector optimization tests and to present such information to the user simultaneously. Such support would only prove useful for cases where multiple sequential vector optimization and/or exercise tests were performed. In such a context, the "before" data would represent output from the last run test and the "after" data would represent output from the current test, notionally conducted in response to adjustments made to the sensor configuration in response to data assessed in the last (i.e. "before") optimization test. A "preview" option/capability could displace the need for any "after" data collection/management as adjustments to the sensor settings within the GUI could be instead used to predict what the response would have been subject to those changed sensor settings. This approach avoids the complication associated with needing "before" and "after" exercise regimens to be matched in exertion, body motion, and duration as a means to best facilitate comparisons of sensor configuration settings.

Furthermore, according to an embodiment, the system comprises the ability to render the plotted activity response data on any of the accelerometer axes/vectors where data has been gathered, whether acquired in "simultaneous" sequentially scanned methods or if gathered one after another in separate tests within a single implant/programmer follow-up session.

According to yet another aspect, a method for automatically selecting or proposing a vector out of several vectors of a multi-axis accelerometer of an implantable medical device is disclosed, wherein the accelerometer is configured to measure an acceleration of the implantable medical device along said vectors. The method comprises the steps of:
  collecting data (e.g. by the implantable medical device) when the patient's body is oriented in alignment with a pre-defined vector (e.g. during a guided follow-up procedure), wherein the data collected from each of the accelerometer's vectors is indicative of the magnitude of the static acceleration of the implantable medical device in the direction of the pre-defined vector, and
  automatically selecting or proposing a vector of said several vectors that is the one associated with the signal having the largest amplitude among the signals.

The method may further comprise modifying the routine outlined above for vector selection to an adaptive format used between follow-up wherein the device periodically samples information from the available accelerometer axes to develop a running history of (non-static, i.e. dynamic) accelerometer information (in ambulatory conditions) indicative of the relative magnitudes of signaling on the distinct, available axes and (in turn) either actively changes the "best" vector selection based on said gathered history in a dynamic manner or simply makes such history available as an accessible statistic capable of informing the user of possible needs to change the "best" vector to another choice.

According to a further embodiment, the method comprises the further step of receiving the collected data from the implantable medical device or from the monitoring device with a programmer, and assessing the collected data with the programmer to automatically select or propose said vector that is associated with the signal having the largest amplitude among the signals. The medical implantable device may be configured to manage said selection in adaptive embodiments itself where the accelerometer's preferred vector updated to a "best" condition between follow-up.

According to a further embodiment of the method, the system or the programmer comprises a graphical user interface (GUI).

According to a further embodiment, the method comprises the further step of graphically displaying the collected data or information derived from the collected data via the GUI, and/or graphically displaying the selected or proposed vector via the GUI, and/or graphically displaying a picture of the implantable medical device showing the selected or proposed vector via the GUI According to a further embodiment, the method comprises the further step of at least one of:

selecting the proposed vector that comprises the best alignment with the pre-defined vector, through a corresponding input into the GUI, confirming the proposed vector as the selected vector, through a corresponding input into the GUI, initiating an activity test through a corresponding input into the GUI during which activity test the patient performs an exercise for a pre-defined amount of time, and recording the heart rate of the patient and/or the raw activity signal output from the accelerometer by means of the implantable medical device, and adapting a rate of the pacing pulses of the implantable medical device based on an acceleration of the implantable medical device with respect to said selected or proposed vector, displaying the heart rate and/or the raw activity signal output from the accelerometer recorded during the activity test (e.g. as one or more trend plots), changing a therapy program setting of the implantable medical device through a corresponding input into the GUI, and displaying a preview of an expected heart rate for the changed therapy program setting via the GUI.

According to a further aspect, an implantable medical device (IMD) is provided, e.g. an intracardiac pacing system (also called leadless pacemaker), an implantable cardiac monitor (also called loop recorder) or an implantable pulse generator (IPG) for neurostimulation. The IMD may comprise an accelerometer. The accelerometer may be a multi-axis accelerometer which is configured to determine an acceleration vector in more than one axes, e.g. in three axes.

According to yet another aspect, a method is provided. The method may comprise determining a selected acceleration vector out of several acceleration vectors (e.g. out of three acceleration vectors), wherein the selected acceleration vector is aligned with gravitational acceleration. The alignment of the selected acceleration vector with gravitational acceleration may be based on the portion of the acceleration vector being directed in the direction of gravitational acceleration.

The method may be applied to an implantable medical device (IMD) having an accelerometer, e.g. a multi-axis accelerometer.

The features described in regard with the medical system can also be applied to the method and vice versa.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

In the following, exemplary embodiments as well as further features and advantages of the present invention are described with reference to Figures, wherein:

FIGS. 2A and 2B show two orientations of an intracardiac pacemaker for vector selection, FIGS. 5-11 show several views of another graphical user interface (GUI).

DETAILED DESCRIPTION

Figure 1:
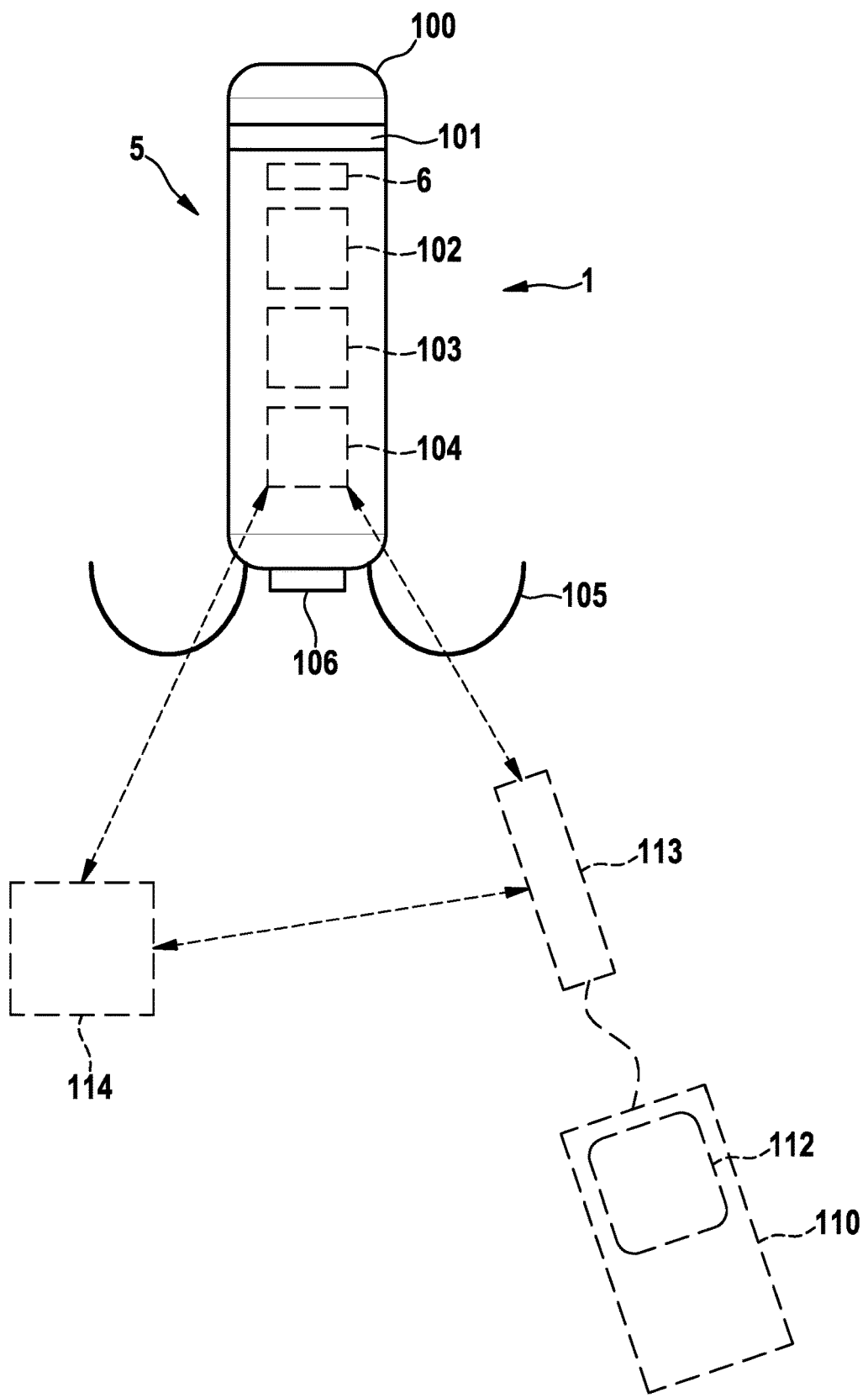
FIG. 1 shows a schematic illustration of an embodiment of a medical system (e.g. an intracardiac pacing system)

FIG. 1 shows a schematic illustration of a medical system 1 comprising at least an implantable medical device (also denoted as implant) in form of an intracardiac pacing system 5 (also denoted intracardiac pacemaker herein). Particularly, the intracardiac pacemaker 5 comprises a housing 100 which surrounds an energy storage 102 (e.g. a battery), an electronic module 103, and a communication unit 104. The housing 100 may comprise titanium or may be made of titanium.

At a distal end of the housing 100, a first electrode 106 (also called pacing electrode) is disposed. In a proximal region of the housing 100, a second electrode 101 (also called sensing electrode) is arranged. The second electrode 101 may be formed as a ring electrode.

The pacemaker system 5 may be fixed to cardiac tissue by a fixation element 105. The fixation element may be formed as a tine. It may comprise Nitinol or may be made of Nitinol. In one embodiment, four tines 105 made of Nitinol may be formed at the distal end of the housing 100.

The energy storage 102 may be configured to provide electrical energy to the components of the intracardiac pacemaker system 10, in particular to the electronic module 103, the communication unit 104, and the first electrode 106.

The electronic module 103 may be configured to perform the functions of a pacemaker, including sensing cardiac events and providing pacing pulses. The electronic module 103 may comprise a processor and memory. Furthermore, the pacemaker 10 preferably comprises a multi-axis accelerometer 6 configured to measure an acceleration of the implantable medical device/pacemaker 10 along e.g. three linear independent vectors/axes of the accelerometer 6.

The communication unit 104 may be configured for communication with an external device (e.g. a programmer) 110. The communication unit 104 may comprise a coil for RF communication (RF—radio frequency).

FIG. 2A shows an example depiction of the "best" vector (here vector 2) for rate adaptation support in an intracardiac pacemaker system (IPS) 5 comprising a multi-axis accelerometer 6. The graphic at the left side of FIG. 2A shows the orientation of the IPS 5 within the patient as assessed by the IPS 5 itself while the plot on the right side of FIG. 2A shows the comparative alignments of the vectors V1, V2, V3 with a pre-defined vector which in the present case is preferably formed by the gravitational vector g (i.e. the direction of gravitational acceleration). Alignment of the vectors V1, V2, V3 with the gravitational vector g may be measured as a percentage, e.g. of the absolute value of the respective vectors V1, V2, V3 with respect to 'g'.

Another orientation of the IPS 5 is shown on the left side of FIG. 2B. The alignment of the acceleration vectors V1, V2, V3 with gravitational acceleration g is shown on the right side of FIG. 2B. Here, vector V1 is the "best" vector for rate adaption.

The IPS 5 may comprise some or all components of the IPS 5 shown in FIG. 1.

One embodiment involves the inclusion of in-IMD (e.g. in-IPS) support for quickly and sequentially scanning through and collecting data from each axis of the multi-axis accelerometer. Ideally, such a capacity could pair with an automatic algorithm and also a triggered response. In other words, in cases where adaptation of the vector selection between follow ups is valuable, the implant 5 could periodically assess all three vectors V1, V2, V3 to ensure that the chosen setting is the "best" or, if the patient exceeds a rate threshold (or otherwise), such conditions could initiate vector selection checks based upon prevailing patient need. The triggered responses would enable in-clinic follow-up assessments where the clinician forces the implant to acquire such information to enable exercise and vector optimization testing.

The orientation of an IPS 5 is highly dependent upon the patient anatomy, the quality and robustness of the device implantation site, and the skills of the implanting physician. There exist few means for prescriptively enforcing an alignment between any single in-device accelerometer axis V1, V2, V3 and the gross patient anatomy. In such an embodiment, the key use of the in-implant accelerometer 6 centers on supporting rate adaptation. To optimally enable such support, with the lowest system overhead, it is notionally best to pick the single axis that aligns with the head-to-toe axis of the patient. Perhaps fortuitously, this axis is also the axis aligned with the gravitational vector g. Whether conducted as an automaticity or as a triggered response, collection of data on all three of the in-device accelerometer's axes/vectors V1, V2, V3 when the patient is sitting or standing, but not otherwise in motion, offers a means for determining which of the multitude of in-system vectors V1, V2, V3 is best aligned with the head-to-toe orientation g of the patient. Such a procedure could facilitate an automated determination of the g vector direction and promote/set that vector (V1, V2, or V3) without necessarily needing to request any user input. In other words, the implant 5 or system 1 itself could readily set and adapt the accelerometer axis choice best suited to rate adaptation. Possible embodiments could even make this process blind to the user and deny the clinician any means to pick another vector that might serve rate adaptation in less robust ways.

In other words, the axis V1, V2, V3 with a response best aligned with 'g' can be determined and reported to the user. One such display of this type is shown in FIGS. 2A and 2B. Here, a visual representation of the implant 5 with an accompanying multi-axis overlay (left side of the figures) and/or a data graphic (right side of the figures) may be used to highlight the vector (e.g. V2 in FIG. 2A and V1 in FIG. 2B) best aligned with the head-to-toe orientation of the patient, i.e. with the gravitational vector g. Selection of such a best aligned vector whether automated by the implant 5 or chosen by the clinician would then best facilitate vector selection well-tuned to support rate adaptation needs in the product. The "best" axis may be color coded in the plots and graphics to promote or to report its selection.

To support an in-clinic exercise test, the implant 5 would ideally collect information on all of the axes/vectors V1, V2, V3 of the accelerometer for a maximum duration of no greater than 30 minutes. The respective information may correspond to a signal of the accelerometer 6 for the respective vector V1, V2, V3 that is indicative of the acceleration of the accelerometer in the respective direction V1, V2, V3. Preferably, such information may be acquired repeatedly, e.g. in a once per minute or half minute frequency type approach where, rather than turning all axes on simultaneously, one axis or vector V1, V2, V3 at a time would be activated to acquire input, cycling through all axes/vectors V1, V2, V3 until the full set is assessed. The data gathered from this work could facilitate the generation of graphics like that found in FIGS. 2A and 2B via relative comparisons of the generated data on each axis V1, V2, V3. In follow-up scenarios computation on these 10 s of minute duration tests may best be performed in a programmer 110 to avoid taxing implant resources.

A variant embodiment which would significantly lower the implant data storage overhead would be one where a temporary monitoring device (e.g. Holter device) 114 could be stationed on the patient's body (nominally over the heart) to collect data related to the signaling observed on each of the axes V1, V2, V3 of the accelerometer 6 (cf. FIG. 1). Such data would be relayed to the monitoring device (e.g. Holter device) 114 via through-body networked communication strategies following the implant's receipt of a test initiation command from the programmer 110. The monitoring device (e.g. Holter device) 114 may then relay the information to a programmer wand 113 at the end of the test's execution. This approach would mean that the implant 5 would simply stream accelerometer data during the test to the monitoring (e.g. Holter) device 114 but not store such information in its on-board memory.

For between-follow-up procedures, the effort would demand an implant-based determination of which vector V1, V2, V3 optimally supports the rate adaptation feature using a shorter data collection period (i.e. substantially less than 10 s of minutes survey). This between-follow-up approach could either adapt/update the primary vector used for rate adaptation over time or be reported as a statistic (without updating the programmed vector) to inform changes at the subsequent follow-up. Such adaptation and/or tracking would prove especially useful for patients with progressive diseases where the heart geometry changes over time and/or conditions where the implant becomes increasingly encapsulated (and potentially less mobile in a given direction).

Figure 3:
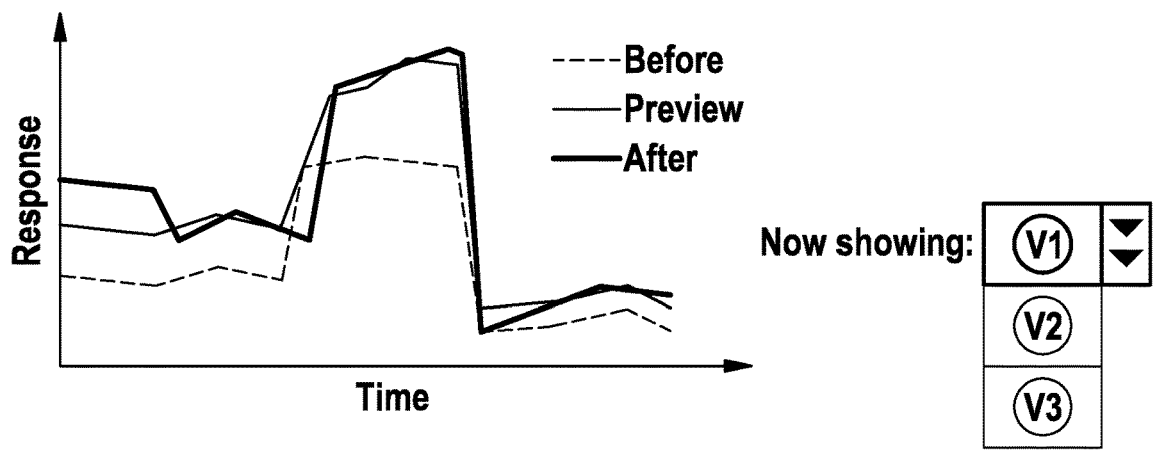
FIG. 3 shows an interface for showing accelerometer response.

Akin to the exercise tests enabled in legacy pocket-based pacemakers, the data acquired during an exercise test at follow-up could be collected and plotted (upon end of test interrogation) as shown in FIG. 3. The response may be represented as rate or activity counts and in one GUI embodiment (GUI—graphical user interface) the clinician can toggle between the two options. Particularly, the GUI 112 can be implemented in the programmer 110 which can be connected to the wand 113 configured for receiving or transmitting data (cf. FIG. 1).

In the depiction shown, one vector V1, V2, V3 is displayed at a time, depending upon which is selected for viewing within the interface (see dropdown menu) 112. The "Before" plot is meant to represent the baseline response of the implant axis V1, V2, or V3 after completing the first exercise test. If changes are made to the test parameters a "Preview" curve is generated to predict the behavior of the implant 5 on the axis V1, V2, or V3 being viewed in light of the edited parameter changes. Such feedback can help the user tune the response of the device 5 and see how it might change the response prior to running a second, parameter-adjusted exercise and vector optimization test. After applying new parameter settings and running the test again, the programmer 110 would retain the last collected data as "Before" and then overlay the new test data as "After". In this way the "Before", predicted (i.e. "Preview"), and "After" data could be shown to best inform the clinician of targeted system responses. As noted earlier, the use/support may prefer excluding support for both "before" and "after" data display. As such, only data from the most recent run would be made available for display and interaction—inclusive of a "preview" capability that would predict what the response would have been subject to changed accelerometer configuration settings.

A variant embodiment of the exercise and vector optimization tests would be to survey only a single, clinician-selectable axis of the multiple axes available within the implant. Doing so would reduce the implant data storage needs to ⅓ of those necessary for strategies that acquire and store data on all three axes. The same interfaces as shown in FIGS. 2A, 2B and 3 may be used for this approach, though the available data would not represent the full set until each of the three axes could be chosen. In such instances, the diagrams at left in FIGS. 2A and 2B might not be available until the full set of tests had been run. In their place, a canonical leadless pacemaker may be shown which included axes that update to reflect the vector chosen by the clinician.

Figure 4:
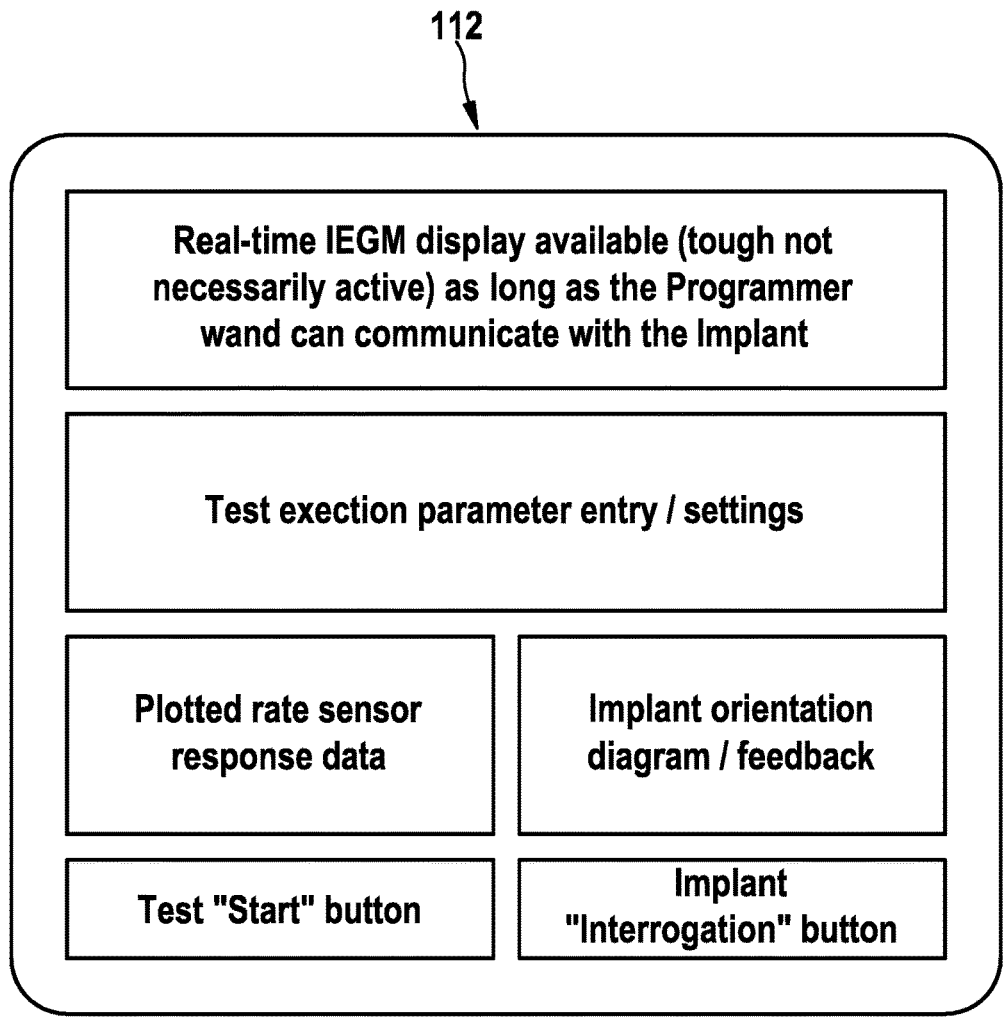
FIG. 4 shows a graphical user interface (GUI)

Some elements associated with GUI support for this feature are illustrated in block format in FIG. 4 where the content detailed in FIG. 3 represents a detailed embodiment of "Plotted rate sensor response data" and FIGS. 2A and 2B represent detailed embodiments of "Implant orientation diagram/feedback". Within this GUI interface 112 for exercise and vector optimization test support, an IEGM (IEGM—intracardiac electrogram) provides real-time feedback while the system is communicating with the implant. The page further offers means for altering/driving test operation via the "Test execution parameter entry/settings" field. Tests are initiated with the "Test 'Start' button" and the results gathered from test execution are supported by bringing the IMD back into communication with the programmer and the use of the "Implant 'Interrogation' button" (which in one embodiment may be automated and thereby not mandate the need for such a button).

Several views of a GUI 112 are shown in FIGS. 5-11 and are further described in the following together with steps which a user may perform in order to determine the "best" vector among the vectors V1, V2, V3.

The user accesses a test page (shown in FIG. 5) prepopulated with parameters from having initially interrogated the device (i.e. the settings in the implant at the start of communication). Within the page, the user can initiate optimal vector selection and (optionally, subsequently) collect activity response data by depressing a "Start Test" button.

Figure 6A:
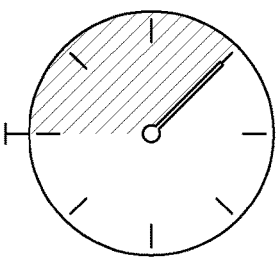
Figure 6B:
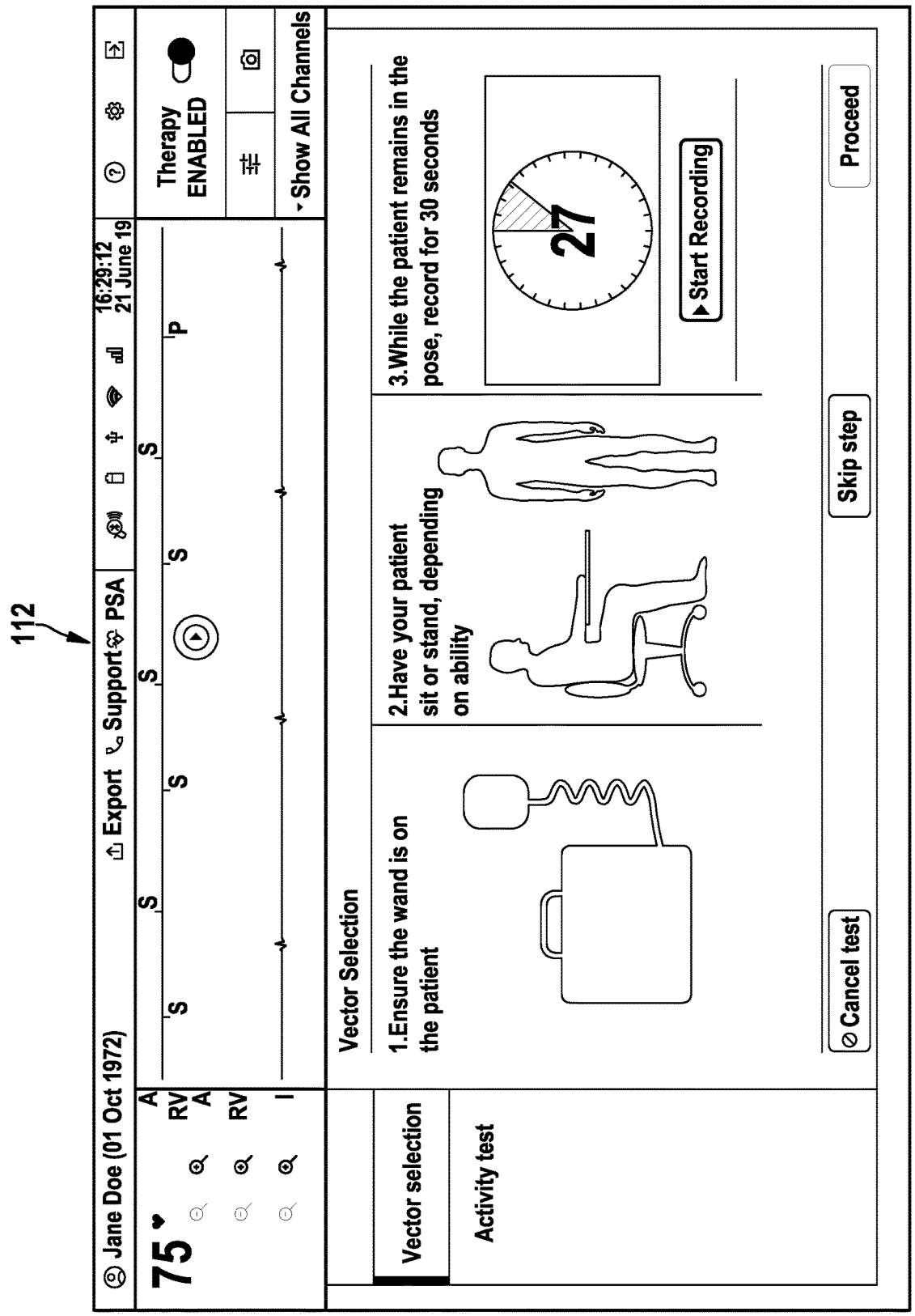

After pressing the "Start Test" button, the GUI 112 instructs the user to sit or stand upright for 30 seconds (FIG. 6A). During this 30 second duration (FIG. 6B) that follows depression of a "Start Recording" button, the implant 5 collects DC measurements (DC—direct current) from each of the three axes/vectors V1, V2, V3 in the implant 5. Assuming offset correction has been managed in the IC design (IC—integrated circuit) for each axis (i.e. trim) V1, V2, V3, the implant returns the DC amplitude for each of the three vectors V1, V2, V3. The programmer 110 takes the largest of the amplitudes of the three vectors V1, V2, V3 and reports it to the user as the preferred vector via the GUI 112.

Figure 7:
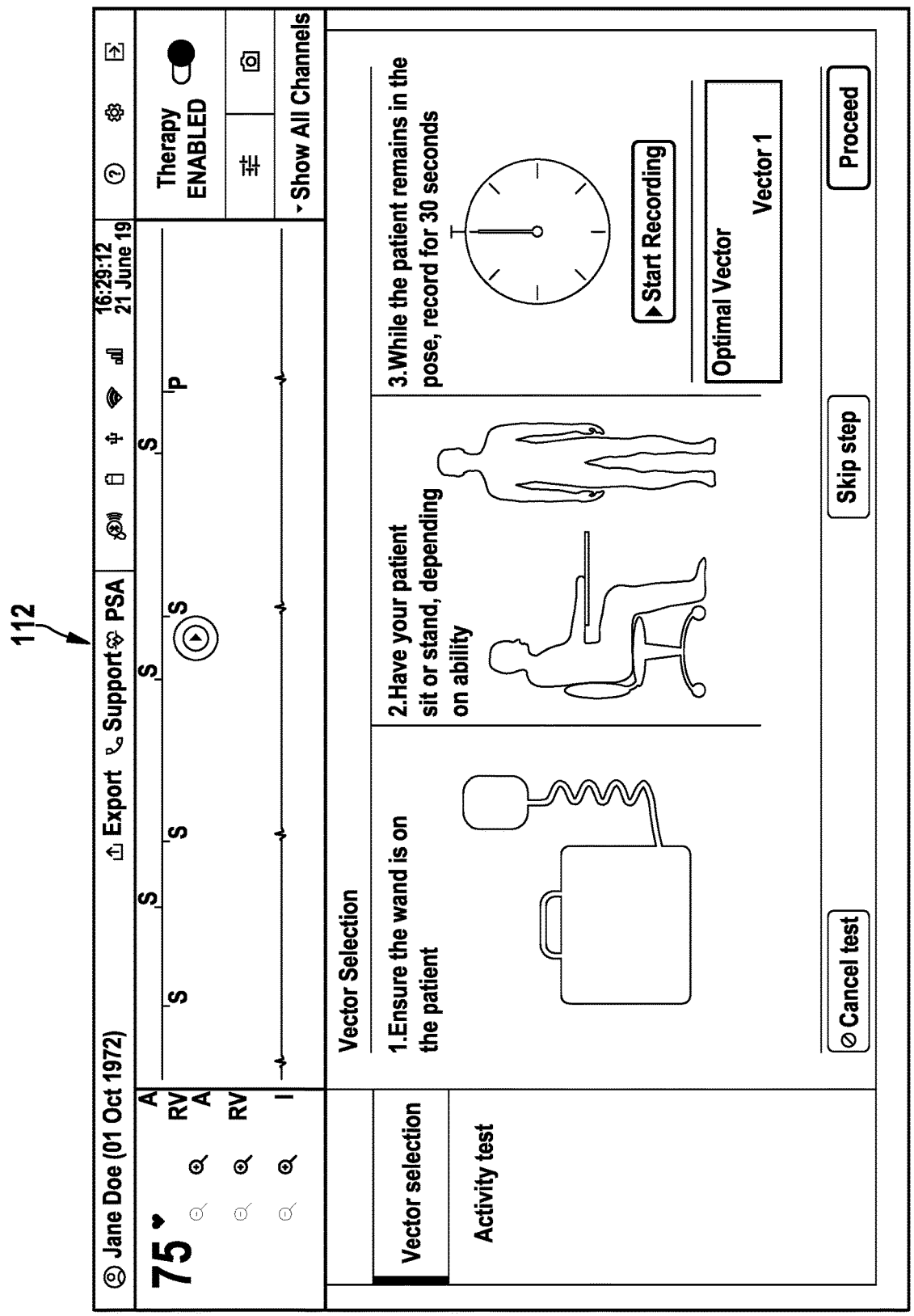
Figure 8:
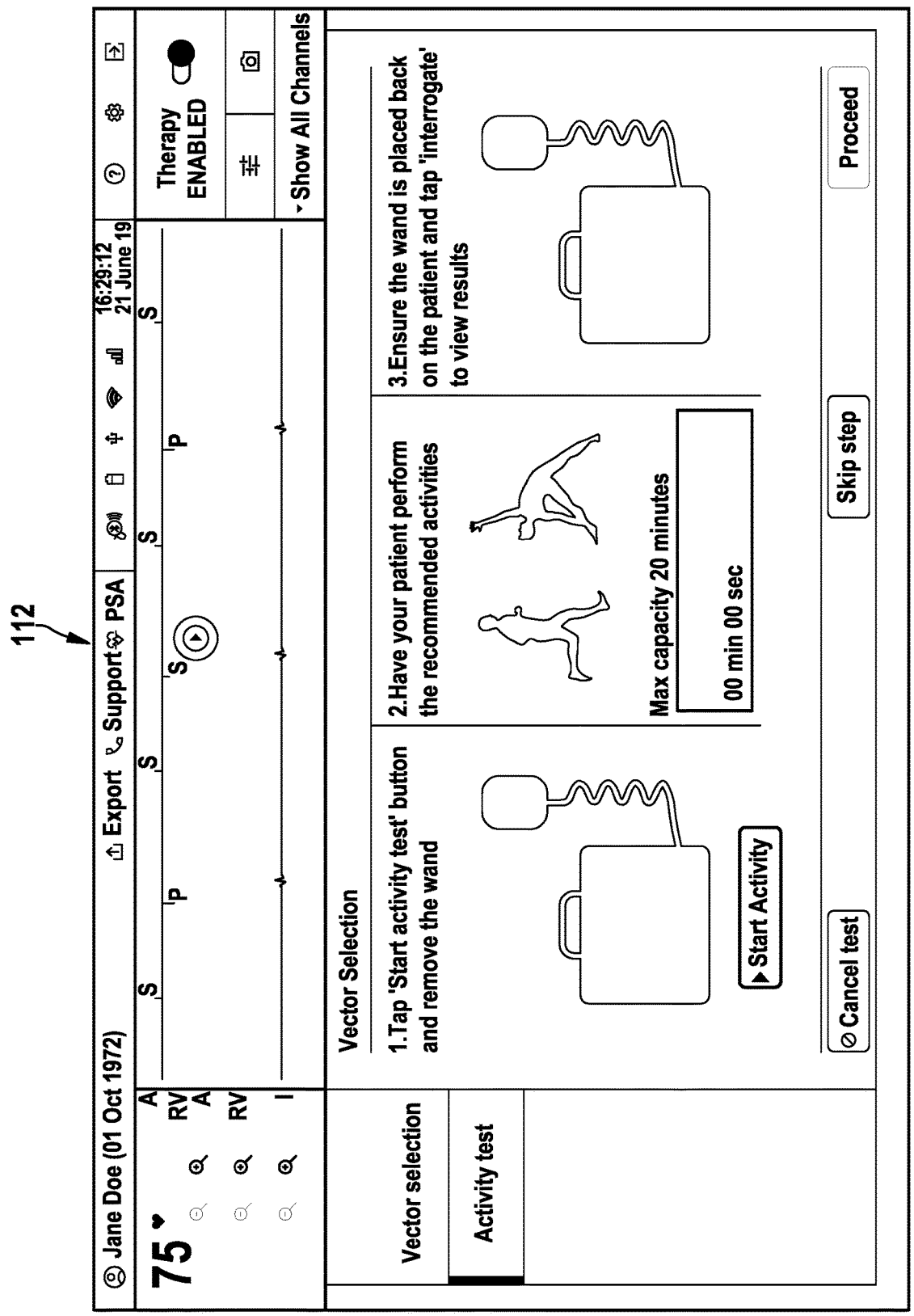
Figure 9:
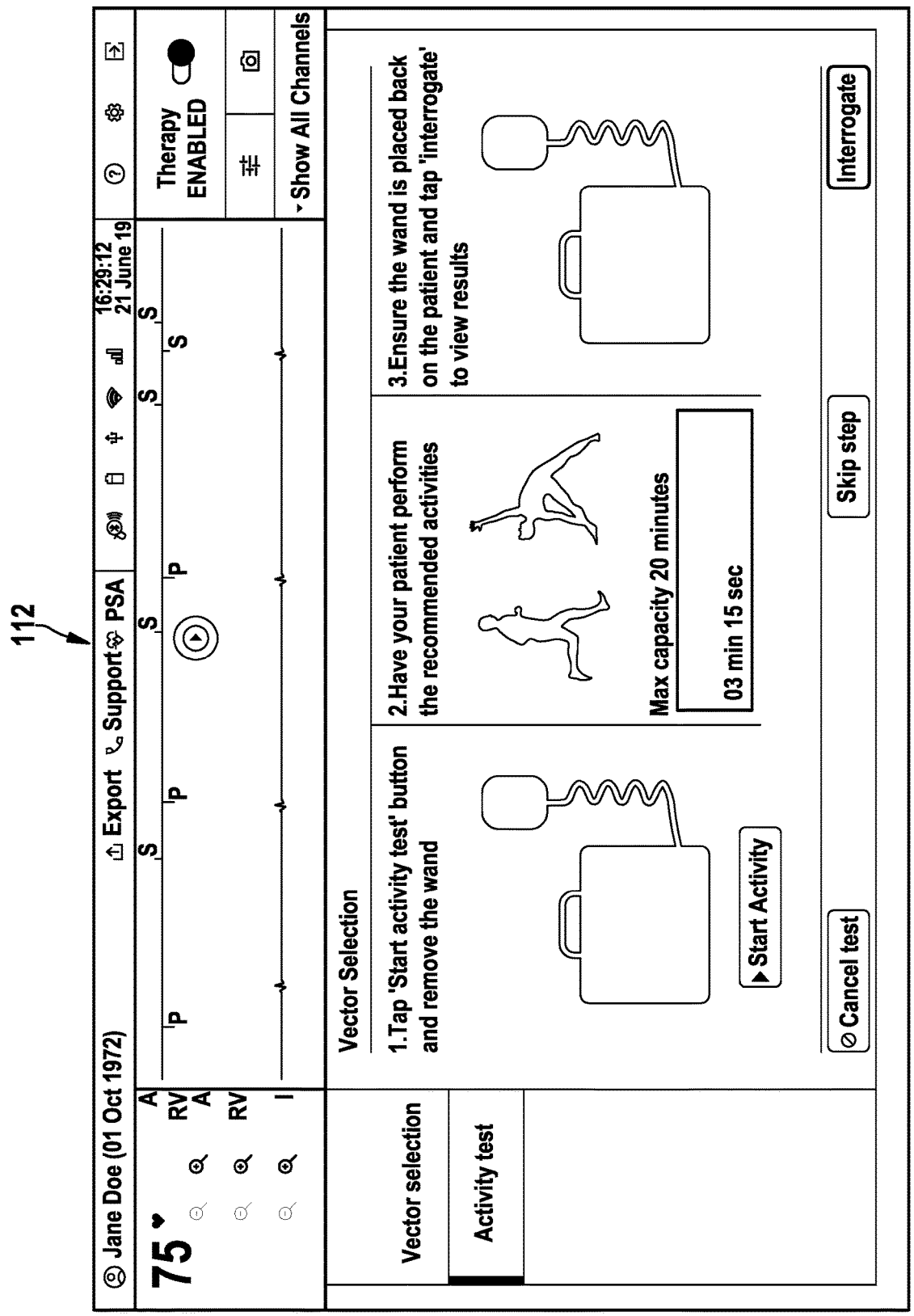

The programmer 110 reports the recommended vector on the right hand side and changes the vector value within the Therapy Program settings on the main page (FIG. 7). If the recommended vector is different from that originally interrogated by the programmer 110 it will be shown in color (e.g. blue) within the Therapy Program settings. The user can, at this point, either leave the recommended vector selection unchanged and run the activity test or change the vector setting and then run the activity test. Running the test is facilitated by user depression of the "Proceed" option which opens the activity test interface (FIG. 8). Whichever vector V1, V2, V3 is selected within the Therapy Program will be the one that the activity test uses to collect data. The user may opt not to even the activity test but to instead simply accept the recommended vector and program the device 5 with it.

The activity test interface offers all pertinent information needed to instruct the patient to conduct the activity test (FIG. 8). After depressing a "Start Activity" button, the user removes the wand 113 (used for communication between the programmer 110 and the implant 5) and moves around doing said exercises. The implant 5 collects upwards of e.g. 20 minutes worth of patient rate/activity data.

After having performed the exercises, the user returns to the programmer 110 and places the wand 113 back over the implant 5. By pressing the "Interrogate" button (FIG. 9), the system 1 collects the rate data that had been collected in the (up to) 20 minute exercise duration.

Figure 10:
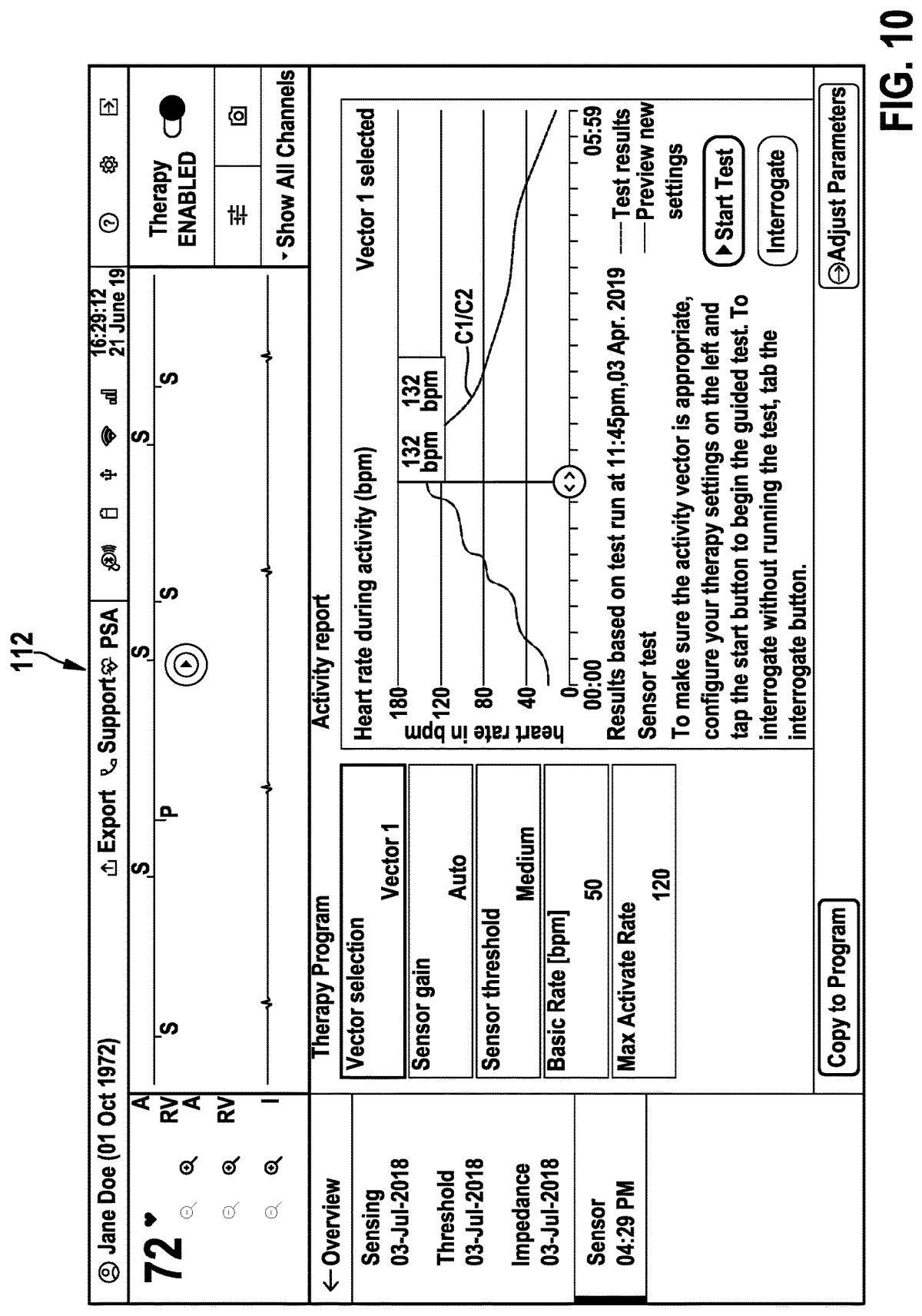

The collected information is plotted on the test page, i.e. in the response to having pressed the "Interrogate" button (FIG. 10). Two curves C1, C2 appear as part of the interrogated display—a preview curve C2 and an original curve C1. At first the two curves C1, C2 are on top of one another and both reflect the response associated with the parameter settings within the Therapy Program portion of the page.

The user adjusts one of the Therapy Program settings to something other than what was used during the Activity Test, e.g. "Auto" to "Low" and the GUI 112 responds to this change (FIG. 11) by changing the preview curve C2 to align with the revised settings in the Therapy Program. In FIG. 3, three curves are shown. In the present embodiment, only the preview curve C2 and the original curve C1 are shown. At any time, if the user likes the settings that exist within the GUI 112 (i.e. could have been done in FIG. 10 too), he/she can send them to the permanent program configuration page by pressing the "Copy to Program" button. The user would then be able to further tweak the therapy and reprogram the device, if necessary.

The selected vector may also be used for fall detection if certain short duration large, large amplitude signaling is detected, e.g. if a patient has seizure and fall, or a pain event, which makes him fall, or has an arrhythmia, which might let him loose consciousness.

Following, a list of further features which may be used in the present invention either alone or in any combination with each other is provided:
- a multi-axis accelerometer within the IMD,
- an ability for the implant to acquire data from any one of the multiple accelerometer axes as an automaticity and/or a triggered response,
- an ability to collect data from each of the multiple accelerometer axes in sequentially scanned format,
- a capacity for the implant to determine the "best" accelerometer axis for targeted feature support (especially rate adaptation) based upon the data collected from the multitude of accelerometer axes,
- an ability to automatically select and adapt the axis used for rate adaptation based upon the preceding bullet point,
- an ability to store data within the implant detailing the activity response of any surveyed accelerometer vector,
- an option to eliminate implant storage for accelerometer axis signaling and instead stream said data to a patient-worn Holter device,
- a patient-worn Holter device capable of collecting the implant-streamed accelerometer axis data for subsequent programmer interrogation,
- a programmer GUI for configuring, initiating, interpreting exercise and vector optimization tests,
- a programmer capacity to interpret data gathered by the implant and/or Holter device and compute "best" accelerometer vector choices for intended feature support (especially rate adaptation),
- a capacity for the programmer to retain information on "Before" and "After" exercise and vector optimization tests and present such information to the user simultaneously,
- an ability to render the plotted activity response data on any of the accelerometer axes where data has been gathered, whether acquired in "simultaneous" sequentially scanned methods or if gathered one after another in separate tests within a single implant/programmer follow-up "session",
an ability to present a data graphic that shows the comparative alignments of vector response data to the 'g' gravitational vector, including the promotion of a single vector as a "best" choice, and
an ability to orient a picture of the device in accordance with information gathered in the preceding bullet point to highlight which vector is best aligned with 'g'.

Furthermore, further embodiments of the present disclosure may have one or more of the following advantages:
accelerometer-based feature support is best aligned with individual patient needs,
facilitates a capacity to adapt to disease state progression and/or encapsulation between follow-up, and
notable truncation of the total clinical time necessary to choose a "best" accelerometer axis to support a given, relevant feature.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. A medical system, comprising at least
an implantable medical device, and
a multi-axis accelerometer comprised by the implantable medical device for measuring an acceleration of the implantable medical device along a plurality of vectors, wherein the multi-axis accelerometer is configured to provide for each vector a signal indicative of the acceleration of the implantable medical device in the direction of the respective vector,
wherein the medical system is configured to assess said signals to automatically select or propose a vector of said plurality of vectors that comprises the best alignment with a pre-defined vector,
wherein the medical system or the implantable medical device is configured to collect data from each of the multiple accelerometer vectors in a sequential fashion so as to cycle through each vector one after the other.

2. The medical system according to claim 1, wherein the implantable medical device is configured to collect data when the implantable medical device is in motion, wherein the collected data comprises for each vector at least an AC signal of the accelerometer being indicative of the acceleration of the implantable medical device in the direction of the respective vector, wherein the selected or proposed vector is the one associated with a DC signal having the largest amplitude among the signals or the one associated with the AC signal having the largest amplitude among the signals.

3. The medical system according to claim 2, wherein the implantable medical device is configured to store the collected data in the medical implant device.

4. The medical system according to claim 2, wherein the medical system comprises a monitoring device configured to be placed outside a body of the patient, wherein the implantable medical device is configured to transmit the collected data to the monitoring device.

5. The medical system according to claim 2, wherein the medical system comprises a programmer configured to receive the collected data from the implantable medical device or from the monitoring device, wherein the programmer is configured to assess the collected data to automatically select or propose said vector that comprises the best alignment with said pre-defined vector.

6. The medical system according to claim 1, wherein the implantable medical device is one of: an intracardiac pacemaker; an implantable cardiac monitor; an implantable pulse generator (IPG) for neurostimulation.

7. The medical system according to claim 1, wherein the implantable medical device is an intracardiac pacemaker, wherein the implantable medical device is configured to generate and apply pacing pulses to the heart of a patient at a rate, wherein the implantable medical device is configured to adapt said rate depending on an acceleration of the implantable medical device with respect to said selected or proposed vector.

8. The medical system according to claim 1, wherein the pre-defined vector is the gravitational vector.

9. The medical system according to claim 1, wherein the medical system or the programmer comprises a graphical user interface.

10. The medical system according to claim 9, wherein the graphical user interface is configured to perform at least one of:
receive input by a user to let the programmer automatically select said vector that comprises the best alignment with the pre-defined vector,
display information on the available vector configurations to guide user insight on the one best aligned with the predefined vector,
receive input by the user to confirm the proposed vector as the selected vector,
receive input by a user to initiate an activity test during which the patient performs an exercise for a pre-defined amount of time and the implantable medical device records the heart rate of the patient and/or the raw activity signal output from the accelerometer, wherein a rate adaption of the pacing pulses by the implantable medical device is based on the acceleration of the implantable medical device with respect to said selected or proposed vector,
display the heart rate and/or raw activity signal output recorded during the activity test,
receive input by a user to change a therapy program setting of the implantable medical device, and
display a preview of an expected heart rate response for the changed therapy program setting.

11. The medical system according to claim 1, wherein the graphical user interface is configured to graphically display the collected data or information derived from the collected data, and/or to display the selected or proposed vector, and/or to display a picture of the implantable medical device showing the selected or proposed vector.

12. A method for automatically selecting or proposing a vector of several vectors of a multi-axis accelerometer of an implantable medical device, wherein the accelerometer is configured to measure an acceleration of the implantable medical device along said vectors, and wherein the method comprises the steps of:
collecting data when a patient's body is oriented in alignment with a pre-defined vector, wherein the data collected from each of the accelerometer's vectors is collected in a sequential fashion by cycling through each vector one after the other and the data is indicative of the magnitude of a static acceleration of the implantable medical device in the direction of the pre-defined vector, and
automatically selecting or proposing a vector of said several vectors that is the one associated with the signal having the largest amplitude among the signals.

* * * * *